US012527974B2

United States Patent

(12) United States Patent
Osinga-Blättermann et al.

(10) Patent No.: US 12,527,974 B2
(45) Date of Patent: Jan. 20, 2026

(54) METHOD TO DETERMINE A PATIENT DOSE DISTRIBUTION AND CORRESPONDING RADIATION DOSIMETRY APPARATUS

(71) Applicants: PTW-Freiburg Physikalisch-Technische Werkstätten Dr. Pychlau GmbH, Freiburg (DE); Stichting het Nederlands Kanker Instituut-Antoni van Leeuwenhoek ziekenhuis, Amsterdam (NL)

(72) Inventors: Julia-Maria Osinga-Blättermann, Schallstadt (DE); Igor Olaciregui Ruiz, Amsterdam (NL)

(73) Assignees: PTW-Freiburg Physikalisch-Technische Werkstätten Dr. Pychlau GmbH, Freiburg (DE); Stichting het Nederlands Kanker Instituut-Antoni van Leeuwenhoek ziekenhuis, Amsterdam (NL)

( * ) Notice: Subject to any disclaimer, the term of this patent is extended or adjusted under 35 U.S.C. 154(b) by 280 days.

(21) Appl. No.: 17/876,807

(22) Filed: Jul. 29, 2022

(65) Prior Publication Data

US 2023/0033009 A1 Feb. 2, 2023

(30) Foreign Application Priority Data

Jul. 29, 2021 (EP) .................................... 21188576

(51) Int. Cl.
*A61N 5/10* (2006.01)

(52) U.S. Cl.
CPC ......... *A61N 5/1071* (2013.01); *A61N 5/1039* (2013.01); *A61N 2005/1076* (2013.01)

(58) Field of Classification Search
CPC .......... A61N 2005/1076; A61N 5/1075; A61N 5/1071; A61N 5/1072; A61N 5/103; A61N 5/1064; A61N 5/1065; A61N 5/1068; A61N 5/1069
See application file for complete search history.

(56) References Cited

U.S. PATENT DOCUMENTS

2014/0105355 A1* 4/2014 Toimela .............. A61N 5/1064 382/132
2020/0134885 A1* 4/2020 Yang ........................ G06T 7/11

OTHER PUBLICATIONS

Wendling M, et al. In aqua vivo EPID dosimetry. Med Phys 2012;39:367-77. (Year: 2012).*
Brualla, L., Rodriguez, M. & Lallena, A.M. Monte Carlo systems used for treatment planning and dose verification. Strahlenther Onkol 193, 243-259 (2017). (Year: 2017).*
(Continued)

*Primary Examiner* — David J Makiya
*Assistant Examiner* — Miya Downing
(74) *Attorney, Agent, or Firm* — Volpe Koenig

(57) ABSTRACT

In a method to determine a patient (radiation) dose distribution (13), it is provided to calculate, from a measured signal (7) of a detector (6) placed behind a region of interest, a dose distribution (11) for a patient-shaped water equivalent phantom (12) and to compute from this a patient dose distribution (13) that takes into account inhomogeneities of a matter distribution of the patient (4).

16 Claims, 8 Drawing Sheets

(56) References Cited

OTHER PUBLICATIONS

Watson PG, et al. Implementation of an efficient Monte Carlo calculation for CBCT scatter correction: phantom study. J Appl Clin Med Phys. Jul. 8, 2015;16(4):216-227. (Year: 2015).*
Wendling Markus et al: "EPID dosimetry", Medical Physics, AIP, Melville, NY, US, vol. 39, No. 1, pp. 367-377, Jan. 1, 2012 (Jan. 1, 2012).
Essers M. et al: "The accuracy of CT-based inhomogeneity corrections and in vivo dosimetry for the treatment of lung cancer", Radiotherapy and Oncology, vol. 37, No. 3, pp. 199-208, Dec. 1, 1995 (Dec. 1, 1995).
Nodehi Mohammad Rasagolrokh et al: "Dosimetric comparison of different inhomogeneity correction algorithms for external photon beam dose calculations", Journal of Medical Physics, [Online] vol. 38, No. 2, pp. 74-81, Jan. 1, 2013 (Jan. 1, 2013).
Mans A et al: "3D Dosimetric verification of volumetric-modulated arc therapy by portal dosimetry", Radiotherapy and Oncology, Elsevier, Ireland, vol. 94, No. 2, pp. 181-187, Feb. 1, 2010 (Feb. 1, 2010).
Van Elmpt W et al: "A literature review of electronic portal imaging for radiotherapy dosimetry", Radiotherapy and Oncology, Elsevier, Ireland, vol. 88, No. 3, pp. 289-309, Sep. 1, 2008 (Sep. 1, 2008).

* cited by examiner

METHOD TO DETERMINE A PATIENT DOSE DISTRIBUTION AND CORRESPONDING RADIATION DOSIMETRY APPARATUS

This application claims priority to EP 21188576.9, which was filed Jul. 29, 2021, was titled Method to determine a patient dose distribution and corresponding radiation dosimetry apparatus, and is incorporated herein by reference as if fully set forth.

TECHNICAL FIELD

The invention concerns a method to determine a patient dose distribution by an external radiation beam from measuring the radiation by a detector during or prior to therapy or after therapy.

BACKGROUND

Modern external beam radiation therapy demands dosimetric methods to perform patient-specific quality assessment.

SUMMARY

It is an object of the invention to provide an improved means for determination of a patient dose distribution during or prior to radiation therapy or after radiation therapy.

To this end, the invention proposes one or more of the features disclosed herein. In particular, the invention proposes a method to determine a patient dose distribution by an external radiation beam from measuring the radiation by a detector during or prior to therapy or after therapy, whereby an algorithm is applied to convert the measured signal of the detector into a dose distribution for a patient-shaped water equivalent phantom in a first step, whereby the dose distribution for the patient-shaped water equivalent phantom is converted in a second step into the patient dose distribution applying a correction based on the inhomogeneous matter distribution of the patient. In the following, the patient-shaped water equivalent phantom is also referred to as water-filled patient. The invention helps to save the user conversion of treatment plan data into water-equivalent data. The user does not have to perform separate calculation of a treatment plan based on the assumption of a water-filled patient in order to compare the treatment plan to a measured dose distribution reconstructed to a water-filled patient is not necessary. This may be used to reduce the effort for patient-specific quality assessment considerably. Further, the invention enables the use of clinically relevant comparison metrics such as patient dose-volume histograms and the verification of the accuracy of the tissue inhomogeneity correction applied by a treatment planning system (TPS). The invention enables the use of the very same approach for reconstructing the patient dose distribution for all treatment sites including those involving large inhomogeneities. This may be beneficial in terms of workflow efficiency.

Water-equivalent matter may be, for example, characterised by behaving, with respect to absorption of radiation, in particular of therapeutically relevant energies such as MeV energies, in the same way as water.

If the measurements are made during treatment, the method determines the actual dose delivered to the patient. If the measurements are made without a patient in the beam, prior or after treatment, the method determines the predicted delivered dose to the patient.

In the beginning of the first step, the measured signal may have been subject to a conversion of a detector intensity into a detected dose. This allows to apply standard algorithms, e.g. taken from calibration data, to obtain the dose distribution for a patient-shaped water equivalent phantom.

The conversion in the second step may be used, inter alia, for a direct comparison of measured/reconstructed patient dose distributions for all treatment sites including those involving large inhomogeneities to those of a treatment plan.

In an advantageous embodiment of the invention the radiation is measured after traversing the patient to reconstruct the patient dose distribution delivered during therapy. Thus, a dose distribution to which a patient has been actually exposed can be calculated. This may be, for example, used in further sessions of a therapy for correction and/or modification of a treatment plan.

In an advantageous embodiment of the invention the radiation is measured free in air to determine the patient dose distribution prior to therapy or after therapy. Thus, a treatment plan can be confirmed and/or verified prior to therapy or after therapy.

As part of the first step, the measured signal by the detector may be transformed into the signal that would have been detected behind a water-filled patient, the so called in aqua dose, by applying an in aqua correction IAC. Thus, calibration data may be used that have been obtained from water-equivalent phantoms. This may be achieved by using an incident angle of radiation according to a treatment plan and/or by using a density information of the patient. For instance, an attenuation of the radiation beam for the incident angle in the patient may be compared to an attenuation of the radiation beam for a patient-shaped water equivalent phantom.

For the purpose of the invention it may be said that a phantom is patient-shaped if, within a determined accuracy, its outer boundary coincides with a patient that is to be examined and/or exposed to the therapy.

The measured signal may be processed in the form of a detected dose as described above.

In an advantageous embodiment of the invention the algorithm to determine the dose distribution of the patient-shaped water equivalent phantom is based on calibration data taken from measurements using water equivalent substance.

For example, the calibration data may have been obtained particular from measurements using photon beams of therapeutically relevant energies. The photon beams may thus have MeV energies. It is advantageous if the energies and radiation type coincide with the ones used during therapy.

In an advantageous embodiment of the invention a radiation propagation algorithm is used. This provides a reliable way to compute the dose distribution.

The radiation propagation algorithm may use, for example, a back-projection algorithm. This may be useful in cases when the detector is placed opposite the radiation source behind the patient or region of interest.

Alternatively, the propagation algorithm may use, for example, a forward-projection algorithm. This may be useful in cases when the detector is placed between the radiation source and the patient or region of interest.

For instance, the radiation propagation algorithm may calculate, from the measured signal which is lower dimensional, a higher dimensional dose distribution. Thus, the detector does not need to be of the same physical dimensions as the patient. Such an algorithm may be based on measured data in a water-equivalent setting.

In many cases, the radiation propagation, e.g. back-projection and/or forward-projection, will convert a measured signal of dimension n into a dose distribution of dimension n+1. For instance, the back-projection may convert a 2D measured signal into a 3D dose distribution.

For instance, a 3D dose distribution for the water-filled patient may be calculated by propagating a 2D measurement signal or its converted in aqua values into the patient-shaped water equivalent phantom.

In an advantageous embodiment of the invention the inhomogeneous matter distribution contains a density distribution information of the patient. Thus, anatomical information, taken from e.g. CT measurements, may be used.

In an advantageous embodiment of the invention the measured signal is propagated, e.g. back-projected and/or forward-projected, into the patient-shaped water-equivalent phantom per radiation beam angle (e.g. gantry angle). This allows to calculate the dose distribution for the water-filled patient angle-wise.

In an advantageous embodiment of the invention the dose distribution for the water-filled patient may be accumulated for several incident radiation beam angles, e.g. per control point, per beam, per arc or over the sum of all beams and/or arcs. Thus, the impact of individual angles, control points, beams and/or arcs to the total accumulated dose distribution may be determined.

In an advantageous embodiment of the invention the inhomogeneity correction is calculated using an amount of incident radiation according to a treatment plan. This allows to use a simulation of the interaction of the incident radiation with the patient's matter on the one hand and with the patient-shaped water equivalent substance on the other hand.

Dose inhomogeneity corrections (DIC) may thus be calculated by using MC (Monte Carlo) numerical methods and/or other dose calculation algorithms for calculation of the 3D dose distribution based on patient-shaped water equivalent phantom and on real patient density distribution information. Thus, a DIC tensor of ratios may be obtained.

In an advantageous embodiment of the invention the dose inhomogeneity correction may be calculated and applied per incident radiation beam angle (e.g. gantry angle), for the sum of several incident radiation beam angles, e.g. per control point, per beam, per arc or for the sum of all beams and/or arcs.

In an advantageous embodiment of the invention the patient dose distribution may be accumulated for several incident radiation beam angles, e.g. per control point, per beam, per arc or over the sum of all beams and/or arcs. Thus, the impact of individual angles, control points, beams and/or arcs to the total accumulated patient dose distribution may be determined.

In an advantageous embodiment of the invention an amount of incident radiation is generated for each incident beam angle according to a treatment plan, in particular the afore-mentioned treatment plan.

In an advantageous embodiment of the invention a treatment plan, for example the treatment plan mentioned earlier, contains data of a cross section (i.e., its shape and/or size) and/or an intensity of the incident radiation beam. Thus, an overall amount of radiation impacting a specific part of a patient may be well determined and/or defined.

In an advantageous embodiment of the invention the accumulated patient dose distribution and/or the patient dose distribution per incident radiation beam angle (e.g. gantry angle), control point, beam and/or arc can be compared, in particular through a computer algorithm, to the planned patient dose distribution according to the treatment plan. Thus, a qualitative assessment of the therapy can be performed.

In general, a beam may be characterized, for example, as a collection of emitted radiation at a certain gantry angle where the individual contributions differ by their respective intensities and/or cross-sections.

A control point may be characterized, for example, as an MLC (Multileaf collimator) position at a particular gantry angle.

An arc may be characterized, for example, as a collection of beam transitions from control point n to control point n+1 at consecutive gantry angles. For example, an arc may cover an angle range of 180°.

In an advantageous embodiment of the invention CT (computed tomography, or X-ray computed tomography) data, or another sufficient source of anatomical information as e.g. cone beam CT (CBCT, cone beam computed tomography) or magnetic resonance imaging (MR) data, of a patient are used in the first step and/or second step. Thus, a 3D model of the patient may be used for dealing with inhomogeneities and/or for converting the measured signal into in aqua dose and/or for radiation propagation, e.g. back-projection and/or forward-projection, into the patient-shaped water equivalent phantom.

1st and 2nd steps as described above may be collectively described as a way of dose reconstruction.

In an advantageous embodiment of the invention a 0D, 1D or 2D detector is used. Various kinds of detectors may be used to obtain a measured signal. Depending on the dimensionality of the detector, different reconstruction methods may be implemented and used.

For instance, the detector may be an electronic portal imaging device (EPID). This allows an easy detection of radiation during therapy and/or for individual incident angles.

Alternatively or in addition, the invention proposes, in another aspect, a radiation dosimetry apparatus with means to perform a method according to the invention, in particular as described above and/or according to any of the method claims.

BRIEF DESCRIPTION OF THE DRAWINGS

The invention will now be described in more detail with reference to a specific example. However, the invention is by no means limited to that example. Other working examples of the invention are conceivable, in particular through a combination of the features of one claim with the features of some of the claims or with various features of the example.

In particular, it is shown in

DETAILED DESCRIPTION

Figure 1:
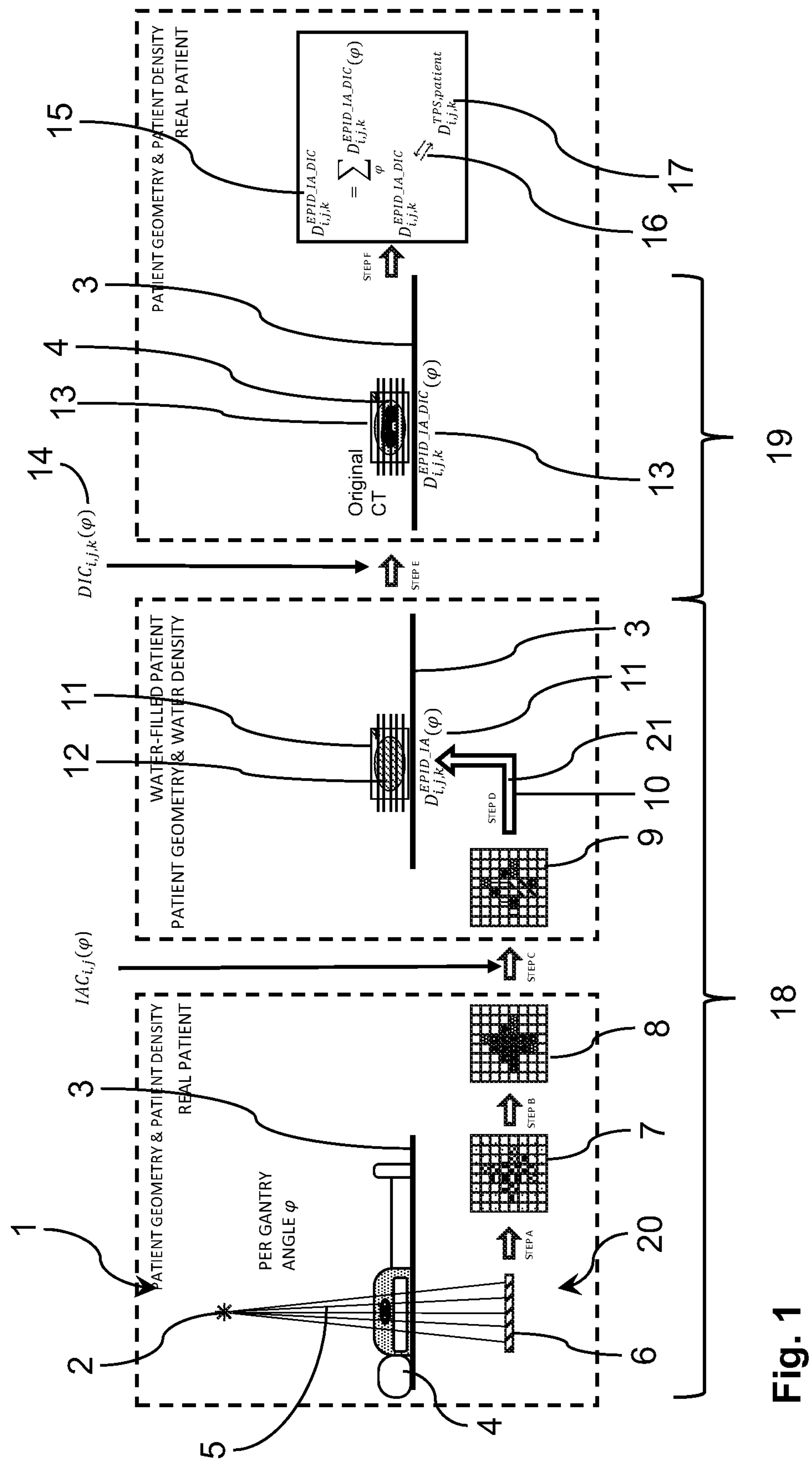
FIG. 1 a schematic view of the various steps of a method according to the invention, FIG. 2 a detailed view of the left box of FIG. 1, FIG. 3 a detailed view of the center box of FIG. 1, FIG. 4 a detailed view of the right box of FIG. 1, FIG. 5 a schematic view showing a calculation of an in aqua correction IAC for conversion of a measured signal into a in aqua dose, FIG. 6 a schematic view showing a calculation of a dose inhomogeneity correction DIC based on the inhomogeneous matter distribution of the patient, FIG. 7 an alternative to FIG. 3, starting from STEP C of FIG. 1, FIG. 8 an alternative to FIG. 4, starting from STEP F' of FIG. 7, and FIG. 9 an alternative arrangement of a detector.

FIG. 1 shows a gantry 1 having a radiation source 2, a couch 3 for a patient 4. The radiation source 2 may be rotated about an axis parallel to the patient 4 to position the radiation source 2 in various gantry angles φ relative to the patient 4.

The radiation source 2 generates a radiation beam 5 that is disseminated towards the patient 4 according to a treatment plan. The treatment plan can, for example, define an intensity and/or a cross-section and/or energy of a radiation beam for various gantry angles φ.

Opposite the radiation source 2 there is a detector 6, e.g. a 2D detector like an EPID (Electronic Portal Imaging Device), for detecting an amount of radiation traversing the patient 4. In case of verification before or after patient treatment, the radiation traverses air.

In other examples, the detector may be adapted to record lower dimensional or higher dimensional signals.

The detector 6 in FIG. 1 produces a measured signal 7 that has to be converted, by means of detector-specific data, into a measured dose 8. The measured dose 8 in this example is a 2D field of data.

The detector 6 and a computation unit (not shown) to carry out at least first and second steps described below for a radiation dosimetry apparatus 20.

Using the incident angle or gantry angle φ, treatment planning information and the density information of the patient (e.g. CT data), an in aqua dose 9 is calculated for all gantry angles cp. It may be said that the in aqua dose 9 is the dose, for the measured dose 8, that would have been obtained had the patient 4 consisted of a water equivalent matter.

Figure 5:
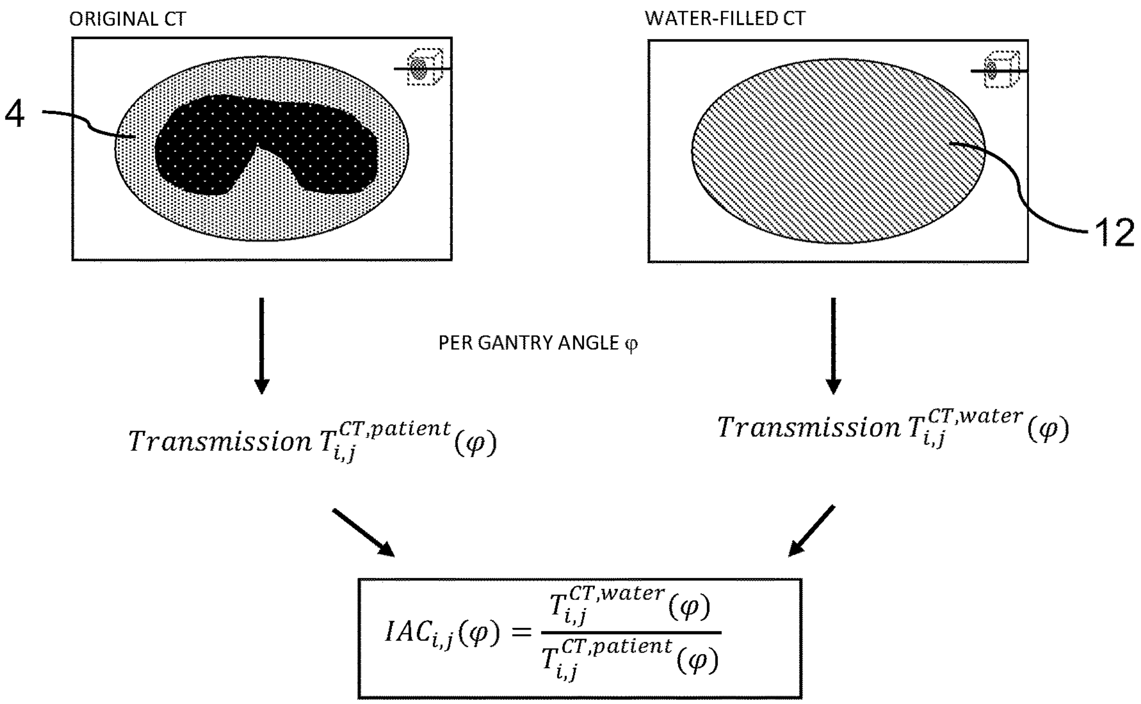

In particular, as an example but not limiting, the primary portal dose distribution $Pr_{i,j}^{EPID}$ (the measured dose 8) is converted into the in aqua primary portal dose distribution $Pr_{i,j}^{EPID\_IA}$ (in aqua dose 9), the equivalent primary portal dose distribution that would be measured behind the water-filled patient. This is achieved by applying an in aqua correction $IAC_{i,j}$ which is defined as the ratio between the primary EPID dose transmission $T_{i,j}^{CT}$ calculated with the water-filled patient and the patient CT data sets (cf. FIG. 5):

$$Pr_{i,j}^{EPID\_IA} = Pr_{i,j}^{EPID} \cdot IAC_{i,j} = Pr_{i,j}^{EPID} \cdot \frac{T_{i,j}^{CT,water}}{T_{i,j}^{CT,patient}} \tag{1}$$

The indices i,j denote pixel position on the 2D detector, which is in this example an electronic portal imaging device.

The in aqua correction factor $IAC_{i,j}$ 'removes' the effect that patient inhomogeneities have on the primary dose detected at EPID level. $T_{i,j}^{CT}$ is calculated using the radiological thickness of the patient t the linear attenuation coefficient of water for a specific beam energy μ and the beam hardening coefficient σ as shown in Eq. (2):

$$T_{i,j}^{CT} = e^{\left(-\mu \cdot t_{ij}^{radiol} + \sigma \cdot \left(t_{ij}^{radiol}\right)^2\right)} \tag{2}$$

The radiological thickness may be computed using properly oriented and/or aligned CT data or other density distribution information of the patient 4.

Then, a back-projection 10 algorithm (as an example of a radiation propagation algorithm) uses the in aqua primary portal dose distribution $Pr_{i,j}^{EPID\_IA}$ to reconstruct (for all gantry angles φ) the delivered dose to the water-filled patient $D_{i,j,k}^{EPID\_IA}$ or dose distribution 11 for the patient-shaped water equivalent phantom 12.

Here, the back-projection 10 algorithm may be based on calibration data taken from measurements using photon beams of therapeutically relevant MeV energies using a water equivalent substance.

This concludes a first step 18 of the method.

From FIG. 1, it can be seen that the first step 18 comprises (sub)steps A through D.

In a second step 19, in particular in a substep E, the dose distribution 11 for the (hypothetical) patient-shaped water equivalent phantom 12 is converted into patient dose distribution 13, for instance by applying a voxel-by-voxel dose inhomogeneity correction $DIC_{i,j,k}$:

$$D_{i,j,k}^{EPID\_IA\_DIC} = D_{i,j,k}^{EPID\_IA} \cdot DIC_{i,j,k} = D_{i,j,k}^{EPID\_IA} \cdot \frac{D_{i,j,k}^{MC,patient}}{D_{i,j,k}^{MC,water}} \tag{3}$$

The indices i,j,k denote points in a 3D region.

Figure 6:
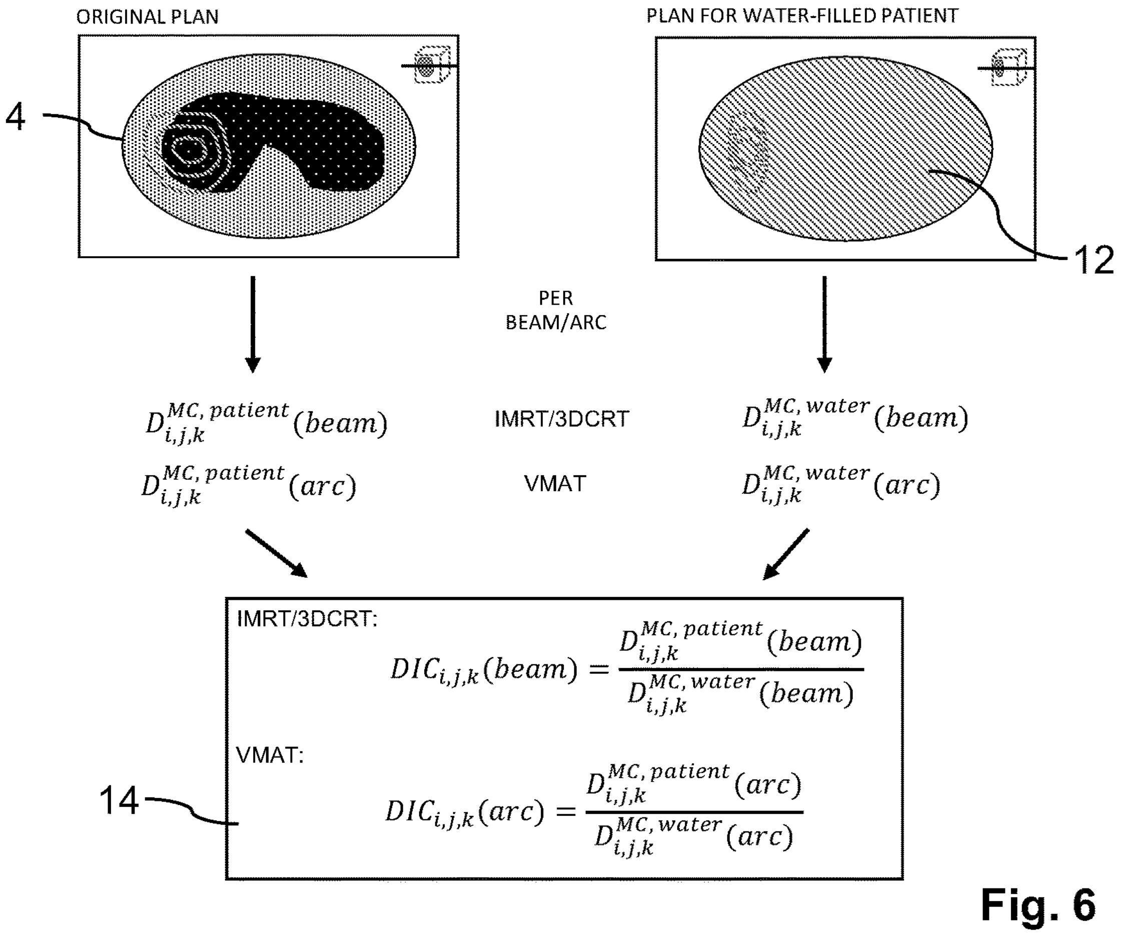

The correction is defined as the ratio between patient and water-filled patient dose calculations, as schematically shown in FIG. 6.

In this example, the Monte Carlo (MC) dose engine SciMoCa of Radialogica LLC, Missouri, USA was used for dose calculation. Other dose engines that are suitable to calculate the dose for inhomogeneous matter distributions accurately may be used as well.

Dose inhomogeneity correction DIC tensors were calculated in this example for each beam in IMRT (Intensity Modulated Radiation Therapy) and 3DCRT (3D Conformal Radiation Therapy) plans and for each arc in VMAT (Volumetric Arc Therapy) plans and applied accordingly.

Figure 4:
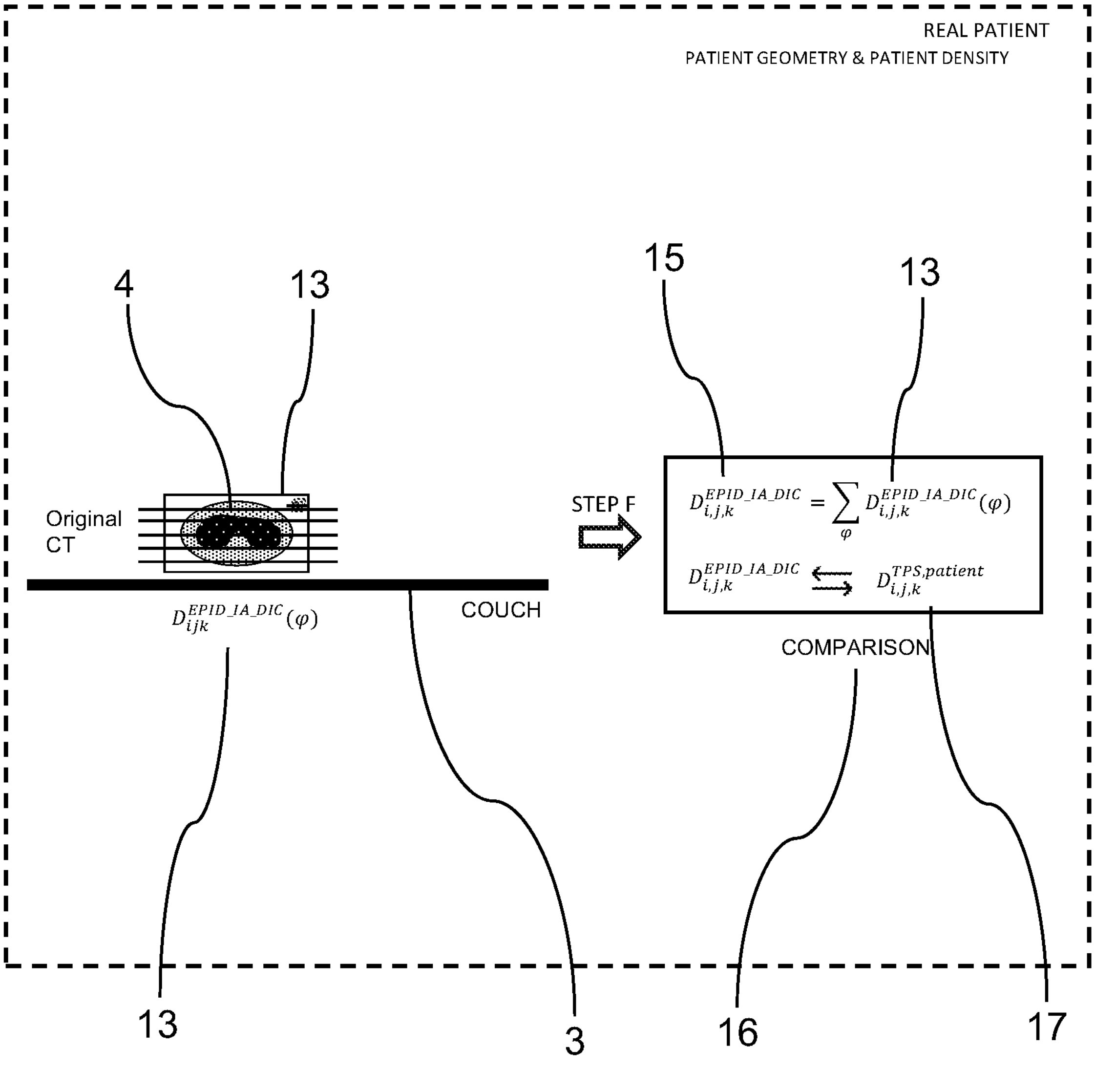

Turning back to FIG. 4, an accumulated patient dose distribution $D_{i,j,k}^{EPID\_IA\_DIC}$ is computed by summing over all beam patient dose distributions in case of IMRT and 3DCRT and all arc patient dose distributions in case of VMAT.

The accumulated patient dose distribution as well as the patient dose distributions per beam/arc may be compared, in a computer-assisted comparison 16, to the corresponding accumulated dose distribution and/or the corresponding beam/arc dose distributions 17 from a treatment plan.

It can be seen from the figures that the measured signal 7, the measured dose 8 and the in aqua dose 9 are 2D data fields corresponding to 2D measurements, while dose distributions 11, 13, 15, and 17 after the back-projection 10 comprise 3D data fields corresponding to spatial dose distributions.

Hence, the back-projection 10 generates a higher dimensional data field from a lower dimensional one, in particular through a simulation or computation of the course of incident radiation. For this, a physical model of the radiation process can be used.

In general, the physical method or computation algorithm is adapted to measurements using photon beams of therapeutically relevant, viz. at MeV energies.

In other examples, detectors that generate data fields of dimensionality below 2 or above 2 will be used.

In another example, the method as described above is performed without a patient 4 on the couch 3. In other words, the measured signal 7 of the detector 6 corresponds to the interaction of the incident beam 5 with air.

This will allow to reconstruct a dose distribution 11 for the patient-shaped water equivalent phantom 12 as described above.

The resulting patient dose distribution 15 may be used to verify a planned dose distribution 17 prior to therapy or after therapy.

Figure 7:
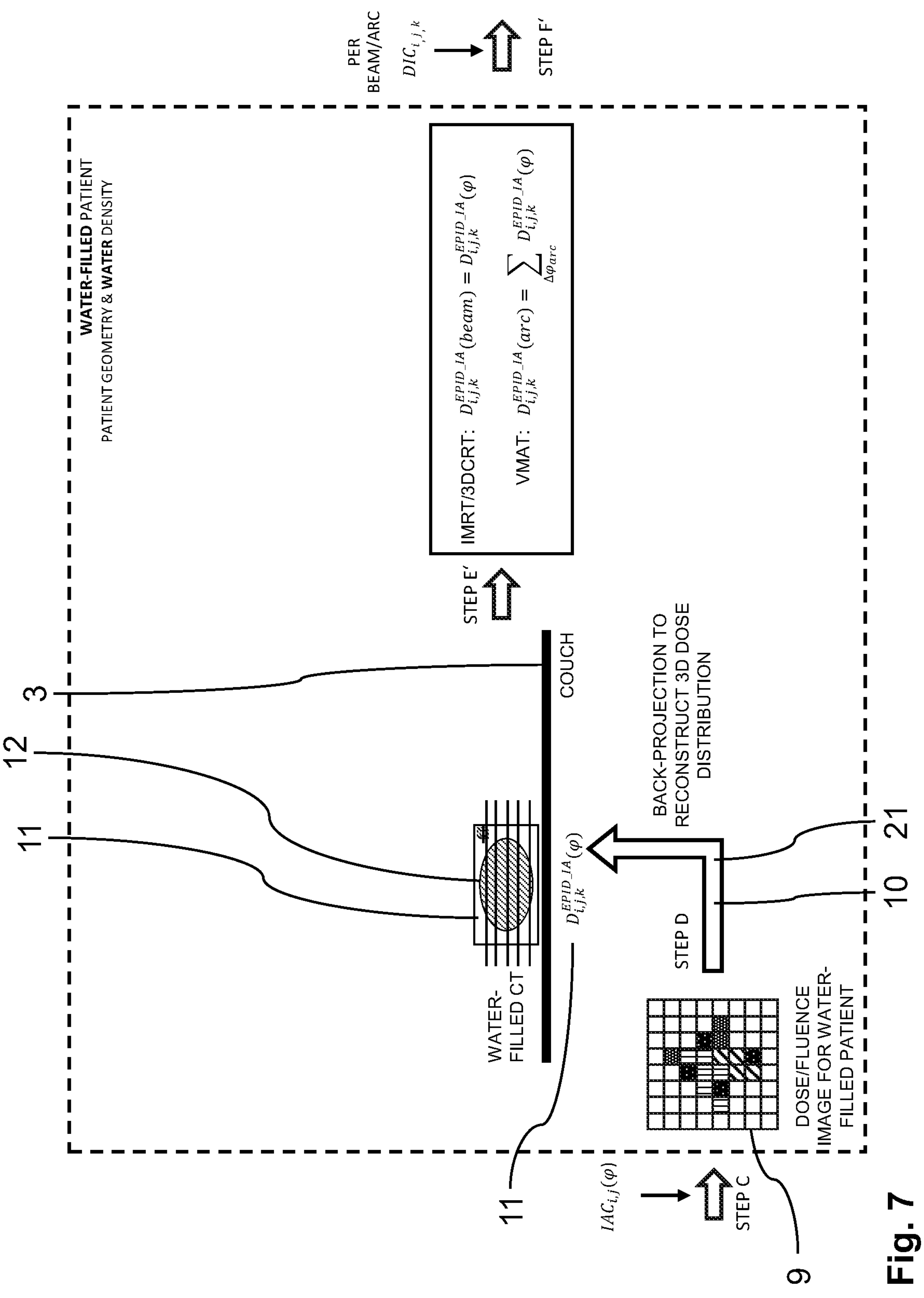

FIG. 7 shows an alternative example of a method according to the invention. The diagram of FIG. 7 may be thought of as setting in at STEP C in FIG. 1, thereby replacing the box of FIG. 2. Structurally or functionally similar or identical elements will be denoted by reference numerals as in FIGS. 1 and 2. Thus, explanations given in the context of FIGS. 1 and 2 are applicable to FIG. 7 as well.

Figure 2:
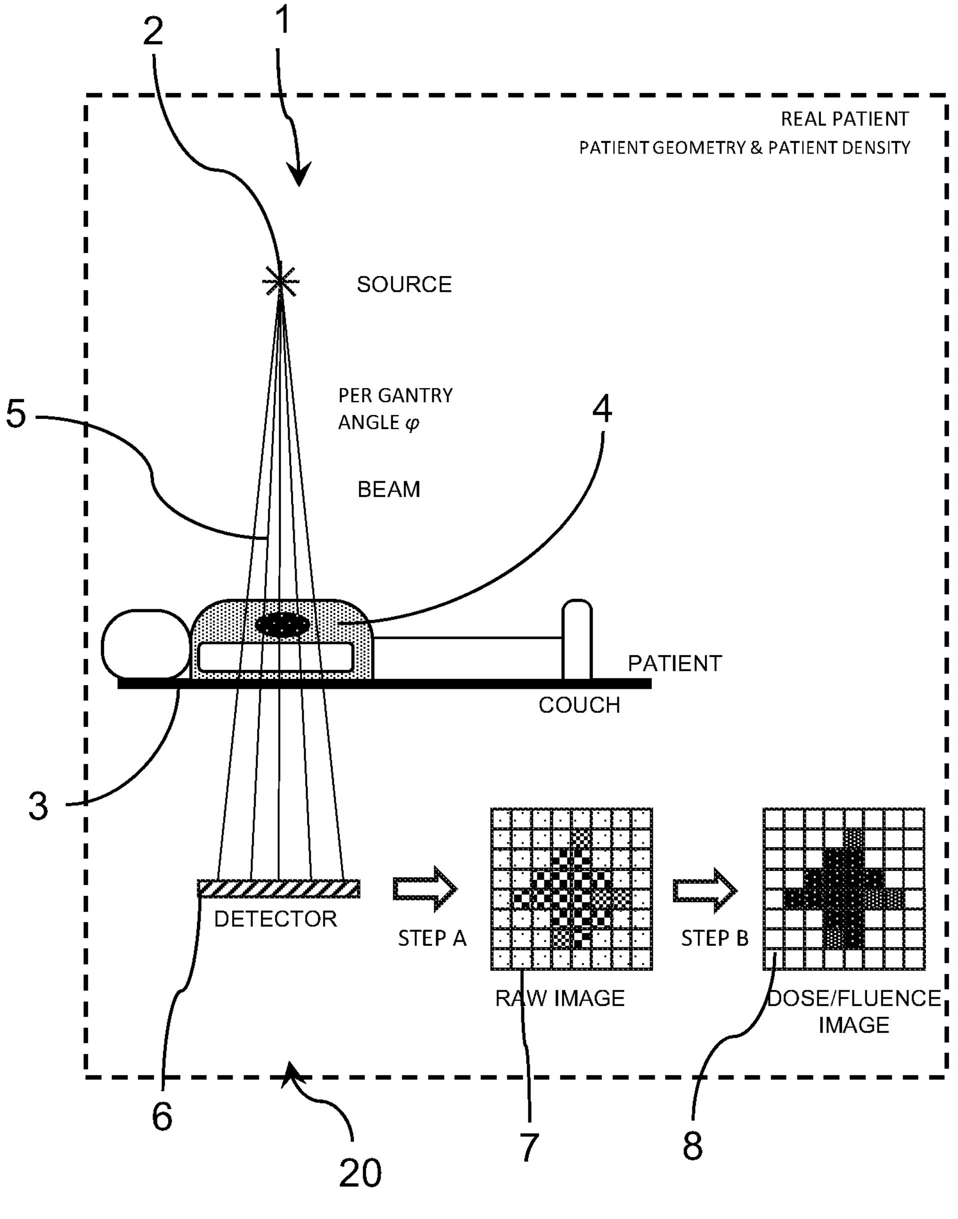

FIG. 7 differs from FIG. 2 in that, in a substep E', the dose distribution 11 for the (hypothetical) patient-shaped water equivalent phantom 12 is summed, or accumulated, over a beam, e.g. for IMRT/3DCRT type therapies, or over an arc, e.g. for VMAT type therapies, before, in a substep F', dose inhomogeneity corrections $DIC_{i,j,k}$ will be applied.

In other words, therefore, $D_{i,j,k}^{EPID\_IA}(\varphi)$ was accumulated, in this example, per arc for VMAT plans and per beam with respect to IMRT or 3DCRT plans.

To this end, the dose inhomogeneity corrections have been computed for a beam or an arc, respectively, such that, for example, an angular resolution of the dose inhomogeneity correction $DIC_{i,j,k}$ matches an angular resolution of the accumulated dose distribution $D_{i,j,k}^{EPID\_IA}(arc)$.

Figure 3:
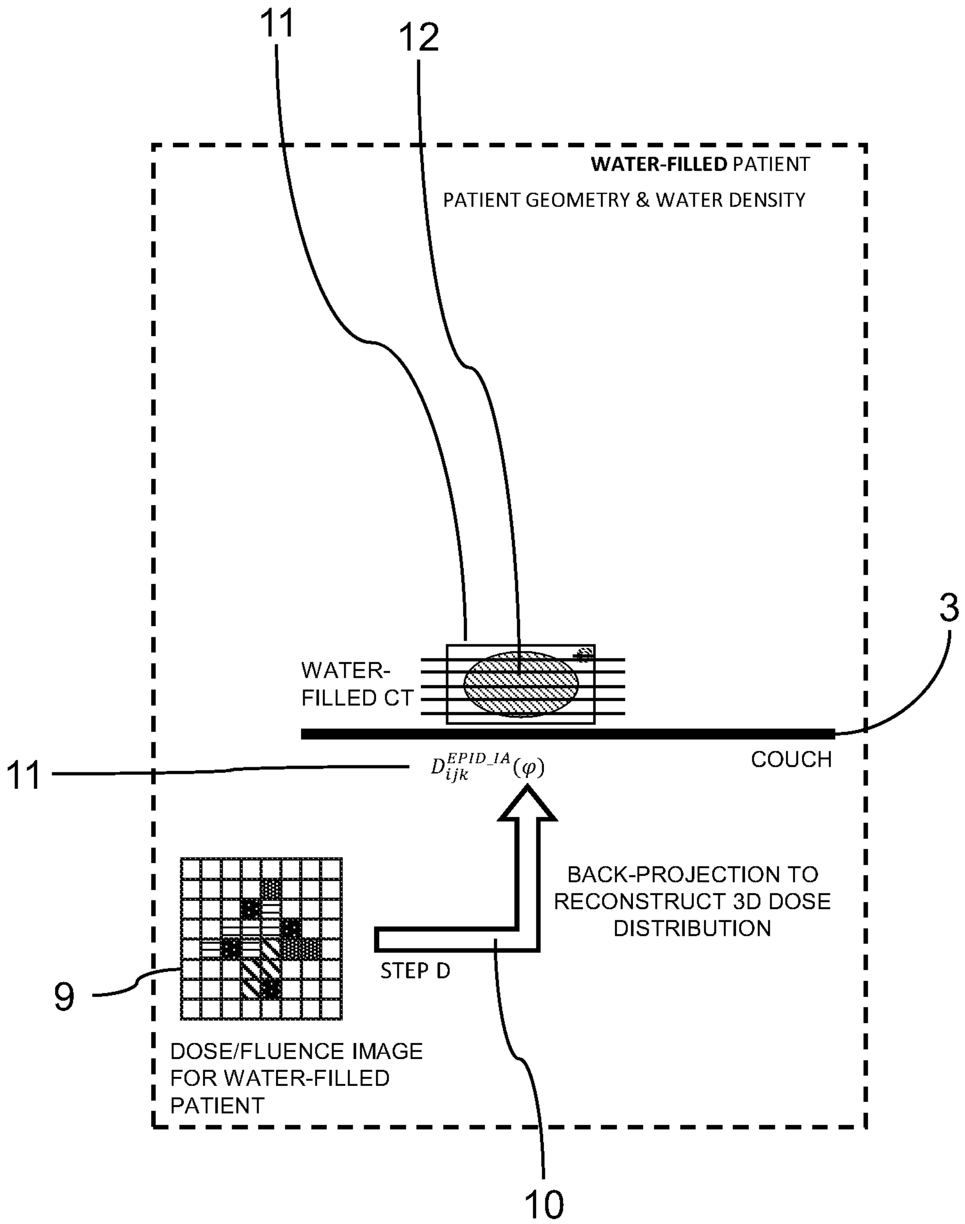
Figure 8:
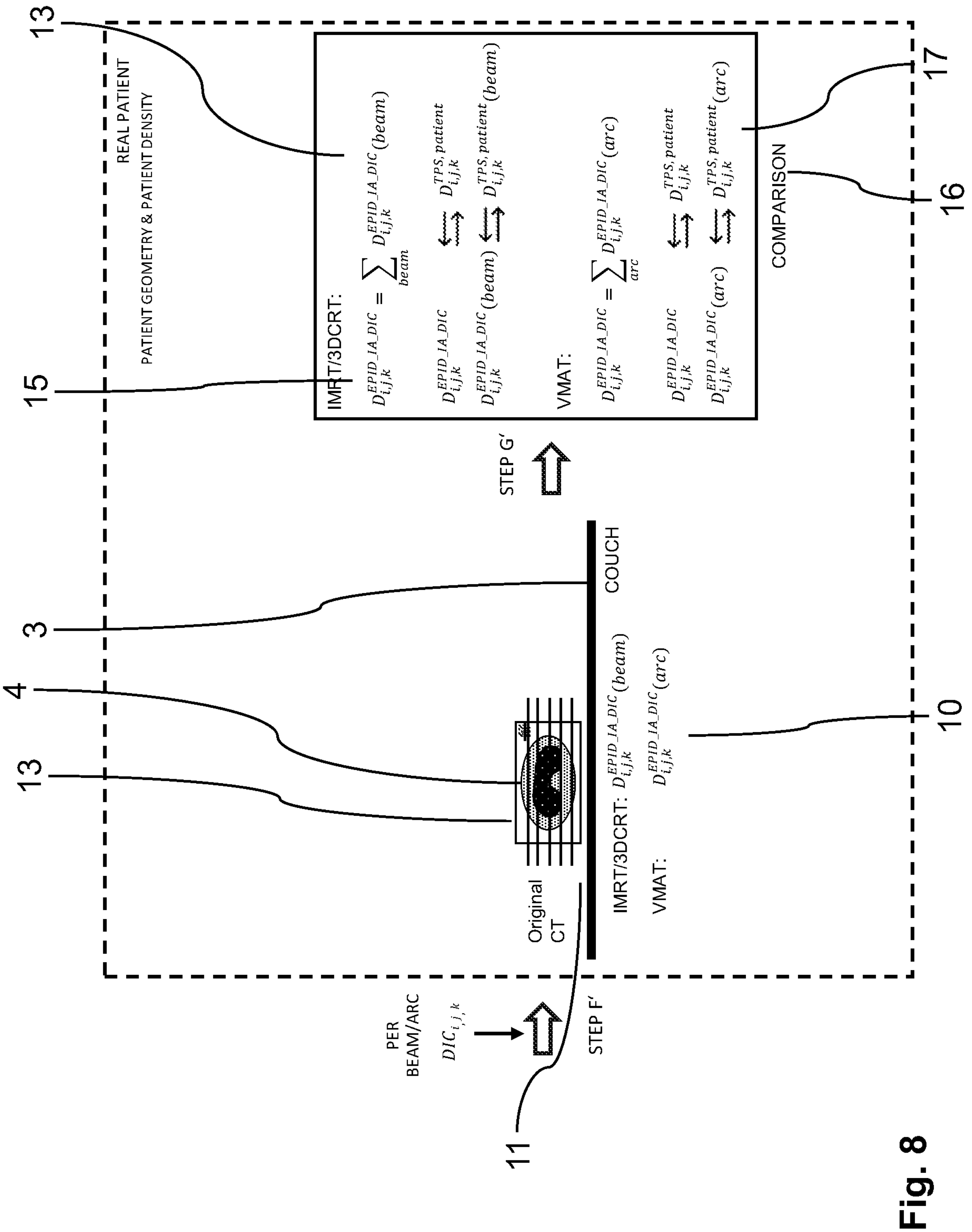

Correspondingly, FIG. 8 shows a variant of FIG. 3 that follows substep F' of FIG. 7. It can be seen that a comparison of measured dose distributions to a treatment plan 17 can be performed per beam or per arc, depending on the type of therapy, or for total accumulated values over all beams or arcs.

Figure 9:
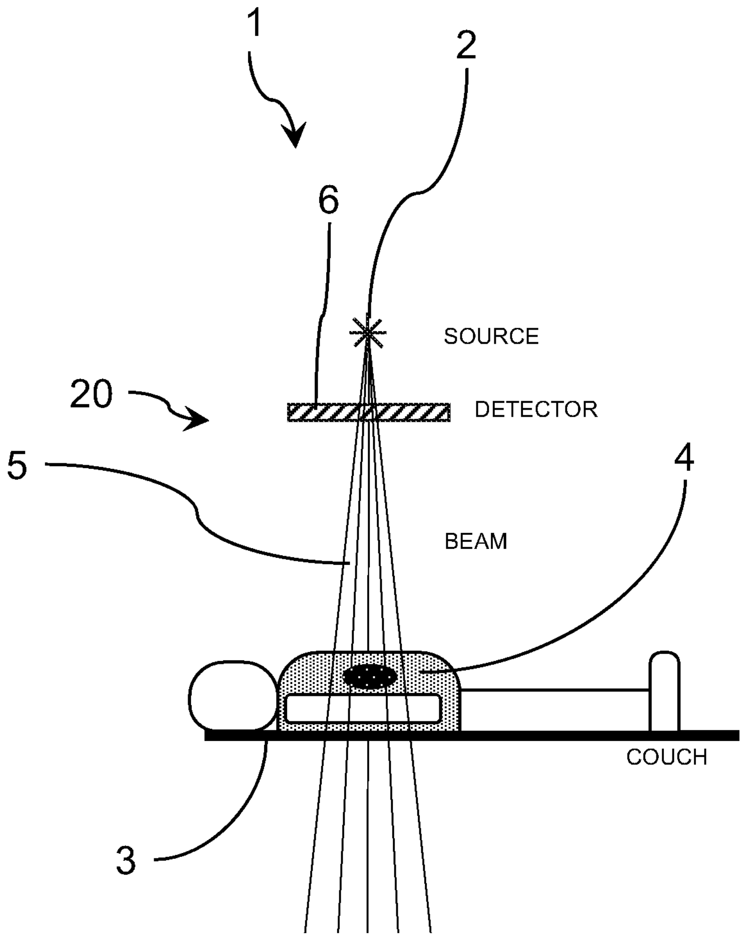

FIG. 9 shows a schematic view of an alternative example for a radiation dosimetry apparatus 20. Again, structurally and/or functionally identical or similar elements are denoted as in FIGS. 1 and 2. Thus, explanations given to FIGS. 1 and 2 may be read together with FIG. 9 as well. The arrangement of FIG. 9 may, for example, replace the one of FIGS. 1 and 2.

The arrangement of FIG. 9 differs from FIGS. 1 and 2 in that, inter alia, the detector 6 is located between radiation source 2 and patient 4.

Thus, substep D in FIG. 1, 2 or 7 will not be carried out by a back-projection 10 but by a forward-projection 21 (cf. FIGS. 1 and 7, where forward-projection 21 may replace or complement back-projection 10).

In a method to determine a patient (radiation) dose distribution 13, it is proposed to calculate, from a measured signal 7 of a detector 6 placed behind a region of interest, a dose distribution 11 for a patient-shaped water equivalent phantom 12 and to compute from this a patient dose distribution 13 that takes into account inhomogeneities of a matter distribution of the patient 4.

LIST OF REFERENCE NUMERALS

1 gantry
2 radiation source
3 couch
4 patient
5 radiation beam
6 detector
7 measured signal
8 measured dose
9 in aqua dose
10 back-projection
11 dose distribution for the patient-shaped water equivalent phantom
12 patient-shaped water equivalent phantom
13 patient dose distribution
14 (inhomogeneity) correction
15 accumulated patient dose distribution
16 comparison
17 planned dose distribution
18 first step
19 second step
20 radiation dosimetry apparatus
21 forward-projection

The invention claimed is:

1. A method to determine a patient dose distribution (13) by an external radiation beam (5), the method comprising:

measuring radiation by a detector (6) during or prior to therapy or after therapy;

applying a radiation propagation algorithm to convert a measured signal (7) of the detector into a dose distribution (11) for a patient-shaped water equivalent phantom (12) in a first step (18), wherein the radiation propagation algorithm is a back-projection (10) algorithm; and converting the dose distribution (11) for the patient-shaped water equivalent phantom (12) in a second step into the patient dose distribution (13) by applying a dose inhomogeneity correction (14) based on an inhomogeneous matter distribution of the patient (4), wherein the dose inhomogeneity correction is calculated by using Monte Carlo (MC) numerical methods.

2. The method according to claim 1, further comprising measuring the radiation after traversing the patient (4) to reconstruct the patient dose distribution (13) delivered during therapy.

3. The method according to claim 1, further comprising measuring the radiation free in air to determine the patient dose distribution (13) prior to therapy or after therapy.

4. The method according to claim 1, wherein the radiation propagation algorithm to determine the dose distribution (11) of the patient-shaped water equivalent phantom (12) is based on calibration data taken from measurements using a water equivalent substance.

5. The method according to claim 1, wherein the radiation propagation algorithm calculates a higher dimensional dose distribution (11, 13) from a measured signal (7) which is lower dimensional.

6. The method according to claim 1, further comprising accumulating an angle-wise propagated dose distribution of the patient-shaped water equivalent phantom (12) for several consecutive incident radiation beam (5) angles (φ), per beam, per control point, per arc, or for a sum of all said arcs or said angles or said beams.

7. The method according to claim 1, wherein the inhomogeneous matter distribution contains a density distribution information of the patient (4).

8. The method according to claim 1, further comprising calculating the inhomogeneity correction (14) per incident radiation beam (5) angle (φ), for several consecutive ones of the incident radiation beam angles (φ), per beam, per control point, per arc, or for a sum of all said arcs or said angles or said beams using an amount of incident radiation.

9. The method according to claim 1, further comprising calculating the patient dose distribution (13) per incident radiation beam (5) angles (φ), for several consecutive ones of the incident radiation beam angles (φ), per beam, per control point, per arc, or for a sum of all said arcs or said angles or said beams.

10. The method according to claim 1, wherein at least one of: a) an amount of incident radiation is generated for each incident radiation beam (5) angle (φ) according to a treatment plan or b) the treatment plan contains data of at least one of a cross section or an intensity of the incident radiation beam (5).

11. The method according to claim 1, further comprising comparing the patient dose distribution (15) to a planned patient dose distribution (17) according to a treatment plan.

12. The method according to claim 1, wherein at least one of a CT, daily CBCT, MR data of a patient (4), or treatment planning data is used in at least one of the first step or the second step.

13. The method according to claim 1, wherein at least one of a 0D, 1D, or 2D detector (6) is used.

14. A radiation dosimetry apparatus (20) configured to perform the method according to claim 1.

15. The method according to claim 4, wherein the measurements are taken using photon beams of therapeutically relevant and/or MeV energies.

16. The method according to claim 13, wherein the detector (6) is an electronic portal imaging device.

* * * * *